US012102509B2

United States Patent
Sanders et al.

(10) Patent No.: US 12,102,509 B2
(45) Date of Patent: Oct. 1, 2024

(54) GRANULATING DRESSING FOR LOW EXUDING CHRONIC WOUNDS

(71) Applicant: Solventum Intellectual Properties Company, Maplewood, MN (US)

(72) Inventors: T. Blane Sanders, San Antonio, TX (US); Christopher Allen Carroll, San Antonio, TX (US); Hannah I. Grothues, Pleasanton, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 263 days.

(21) Appl. No.: 16/618,682

(22) PCT Filed: May 24, 2018

(86) PCT No.: PCT/US2018/034468
§ 371 (c)(1),
(2) Date: Dec. 2, 2019

(87) PCT Pub. No.: WO2018/226430
PCT Pub. Date: Dec. 13, 2018

(65) Prior Publication Data
US 2020/0188182 A1      Jun. 18, 2020

Related U.S. Application Data

(60) Provisional application No. 62/517,425, filed on Jun. 9, 2017.

(51) Int. Cl.
*A61F 13/0206* (2024.01)
*A61F 13/00* (2024.01)

(52) U.S. Cl.
CPC .............. *A61F 13/0206* (2013.01); *A61F 2013/00255* (2013.01)

(58) Field of Classification Search
CPC ........ A61F 13/0206; A61F 2013/00255; A61F 13/0216; A61F 2013/0028;
(Continued)

(56) References Cited

U.S. PATENT DOCUMENTS 1,355,846 A    10/1920   Rannells
2,547,758 A     4/1951   Keeling
(Continued)

FOREIGN PATENT DOCUMENTS

AU         550575 B2      3/1986
AU         745271 B2      3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Sarah Al Hashimi
*Assistant Examiner* — Nhu Q. Tran

(57) ABSTRACT

In some non-limiting examples, a system for stimulating tissue growth at a tissue site may include a porous foam and a moisture barrier. The porous foam may include an exterior-facing surface, a tissue contact surface, and a plurality of struts positioned at the tissue contact surface. The plurality of struts may be configured to contact the tissue site and to create tissue deformation at the tissue site without the application of a reduced pressure. The moisture barrier may be configured to cover the exterior-facing surface of the porous foam and to trap moisture at the tissue site. Also provided are other systems, apparatus, and methods suitable for stimulating tissue growth.

11 Claims, 7 Drawing Sheets

(58) Field of Classification Search
CPC .... A61F 2013/00536; A61F 2013/0054; A61F 13/022; A61F 13/00068
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0069863 A1* | 3/2010 | Olson ............... A61M 1/915 604/385.01 |
| 2010/0280428 A1 | 11/2010 | Widgerow et al. |
| 2010/0305526 A1 | 12/2010 | Robinson et al. |
| 2013/0072850 A1* | 3/2013 | Locke ............... A61L 15/22 604/20 |
| 2014/0031771 A1* | 1/2014 | Locke ............... A61M 1/732 156/60 |
| 2014/0163491 A1 | 6/2014 | Schuessler et al. |
| 2014/0296804 A1* | 10/2014 | Hicks ............... A61F 13/05 604/319 |
| 2015/0080788 A1 | 3/2015 | Blott et al. |
| 2016/0015872 A1* | 1/2016 | Luckemeyer ......... A61M 3/022 604/315 |
| 2016/0166744 A1* | 6/2016 | Hartwell ........... A61F 13/00021 604/319 |
| 2018/0296395 A1* | 10/2018 | Kubek ............... A61M 1/90 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |

(56) References Cited

FOREIGN PATENT DOCUMENTS

| | | |
|---|---|---|
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9403214 A2 | 2/1994 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2012168678 A1 | 12/2012 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.

* cited by examiner

GRANULATING DRESSING FOR LOW EXUDING CHRONIC WOUNDS

RELATED APPLICATION

This application claims the benefit, under 35 U.S.C. § 119(e), of the filing of U.S. Provisional Patent Application Ser. No. 62/517,425, entitled "GRANULATING CHRONIC WOUND DRESSING," filed Jun. 9, 2017, which is incorporated herein by reference for all purposes.

FIELD

This application relates generally to medical treatment systems and, more particularly, but not by way of limitation, to apparatus, dressings, systems, and methods that may be suitable for treating a tissue site.

BACKGROUND

Clinical studies and practice have shown that providing a reduced pressure in proximity to a tissue site may augment and accelerate growth of new tissue at the tissue site. The applications of this phenomenon are numerous and may, without limitation, involve wound healing. This treatment may be referred to as "negative pressure wound therapy," "reduced pressure therapy," or "vacuum therapy." Reduced pressure therapy may provide a number of benefits, including migration of epithelial and subcutaneous tissues, improved blood flow, micro-deformation of tissue, and macro-deformation of tissue. These benefits may result in increased development of granulation tissue and faster healing times. Conventional reduced pressure therapy may employ a reduced pressure source and associated system and control components to communicate the reduced pressure to tissue at the tissue site through a manifold or porous device.

Some tissue sites or wounds may not be a candidate for conventional reduced pressure therapy, but may benefit from the increased development of granulation tissue and faster healing times offered by this treatment. Accordingly, improvements to apparatus, dressings, systems, and methods for stimulating tissue growth without the application of reduced pressure and the associated system and control components may be desirable.

SUMMARY

In some illustrative, non-limiting example embodiments, a system for stimulating tissue growth at a tissue site may include a porous foam and a moisture barrier. The porous foam may include an exterior-facing surface, a tissue contact surface, and a plurality of struts positioned at the tissue contact surface. The plurality of struts may be configured to contact the tissue site and to create tissue deformation at the tissue site. Further, the porous foam may be configured to provide a contact force at least between the plurality of struts and the tissue site to create the tissue deformation without the application of a reduced pressure. The moisture barrier may be configured to cover the exterior-facing surface of the porous foam. Further, the moisture barrier may be configured to trap moisture at the tissue site.

Further, in some illustrative, non-limiting example embodiments, a method for stimulating tissue growth at a tissue site may include providing an interactive body. The interactive body may include a tissue contact surface, and the tissue contact surface may include a plurality of struts and a plurality of voids exposed at the tissue contact surface. The method may include positioning the tissue contact surface in contact with the tissue site, and engaging the plurality of struts and the plurality of voids with a tissue at the tissue site to create a contact force on the tissue. Further, the method may include covering the interactive body at the tissue site with a moisture barrier configured to trap moisture at the tissue site, and deforming the tissue at the tissue site by operation of the contact force without an application of a reduced pressure.

Further, in some illustrative, non-limiting example embodiments, a system for stimulating tissue growth at a tissue site may include an interactive body that may be configured to create tissue deformation at the tissue site. The interactive body may include a tissue contact surface, a plurality of struts, a plurality of voids, a tissue interface pattern, and a body mass. The tissue contact surface may be configured to contact the tissue site. The plurality of struts and the plurality of voids may be exposed at the tissue contact surface. The tissue interface pattern may be defined by the plurality of struts and the plurality of voids at the tissue contact surface. The tissue interface pattern may be configured to engage the tissue site, and the body mass may be configured to create the tissue deformation in combination with the tissue interface pattern.

Further, in some illustrative, non-limiting example embodiments, a system for stimulating tissue growth at a tissue site may include a porous foam. The porous foam may include a tissue contact surface and a plurality of struts positioned or exposed at the tissue contact surface. The plurality of struts may be configured to contact the tissue site and to create tissue deformation at the tissue site. Further, the porous foam may be configured to provide a contact force at least between the plurality of struts and the tissue site to create the tissue deformation without the application of a reduced pressure.

Further, in some illustrative, non-limiting example embodiments, the system may include a plurality of voids. The plurality of voids and the plurality of struts may be exposed at the tissue contact surface and configured to engage the tissue site. Further, in some non-limiting example embodiments, the porous foam may include a hydrophobic reticulated polyurethane foam. In some non-limiting example embodiments, the system may include a sealing member configured to provide a sealed space between the sealing member and the tissue site. The porous foam may be configured to be positioned in the sealed space.

Further, in some illustrative, non-limiting example embodiments, a method for stimulating tissue growth at a tissue site may include providing an interactive body comprising a tissue contact surface. The tissue contact surface may include a plurality of struts and a plurality of voids exposed at the tissue contact surface. Further, the method may include positioning the tissue contact surface in contact with the tissue site, and engaging the plurality of struts and the plurality of voids with a tissue at the tissue site to create a contact force on the tissue. Further, the method may include deforming the tissue at the tissue site by operation of the contact force without an application of reduced pressure.

Other aspects, features, and advantages of the illustrative examples will become apparent with reference to the drawings and detailed description that follow.

DETAILED DESCRIPTION OF ILLUSTRATIVE EMBODIMENTS

In the following detailed description of illustrative example embodiments, reference is made to the accompanying drawings that form a part of this disclosure. Other embodiments may be used, and logical, structural, mechanical, electrical, and chemical changes may be made without departing from the scope of this disclosure. Further, the description may omit certain information known to those skilled in the art. The description is also non-limiting, with the appended claims defining the scope of the illustrative embodiments.

Figure 1:
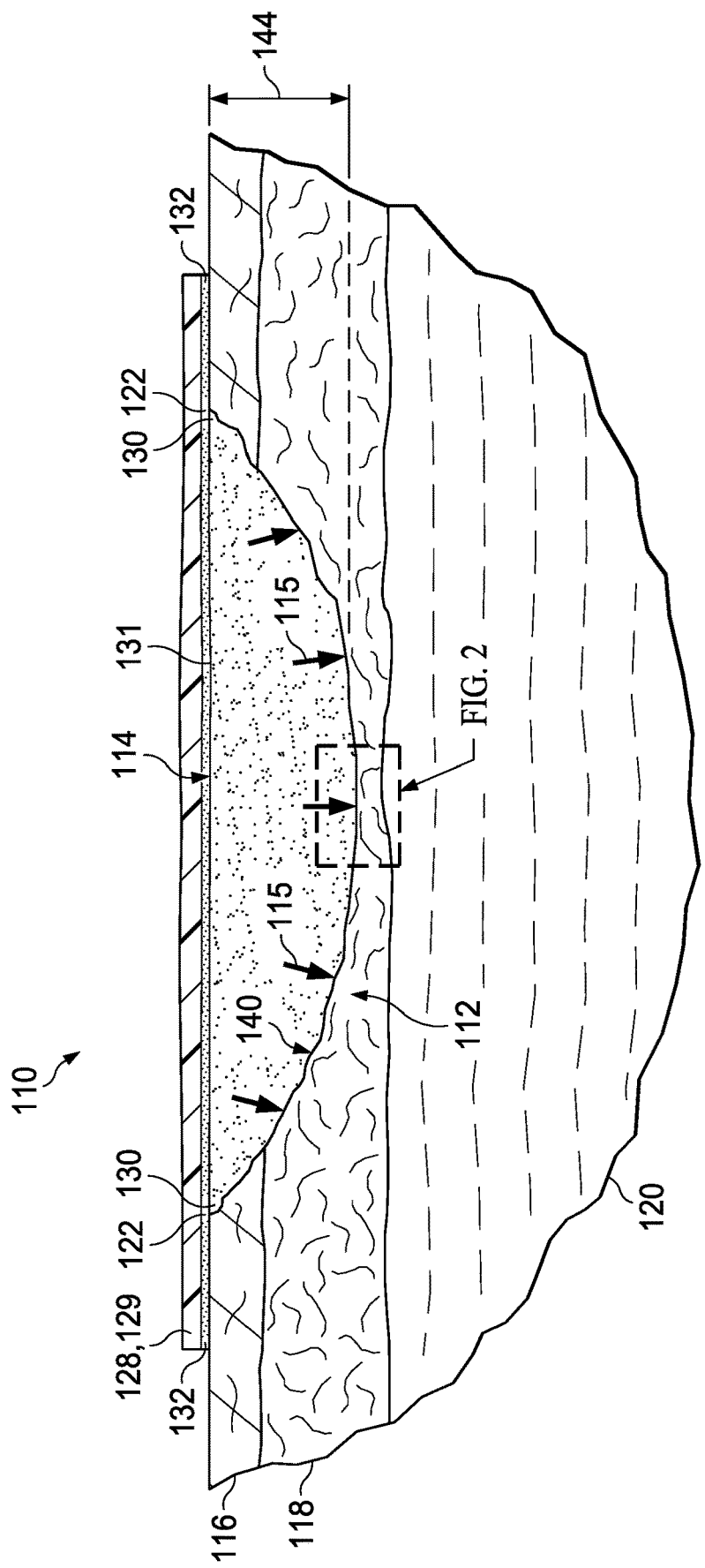
FIG. 1 is a cut-away view of an illustrative example of a system for stimulating tissue growth depicting an illustrative example of an interactive body positioned at a tissue site.

Referring to FIG. 1, in some illustrative, non-limiting examples, a system 110 for stimulating tissue growth at a tissue site 112 may include an interactive body 114 that may be configured to create tissue deformation at the tissue site 112. The interactive body 114 may be configured to create the tissue deformation by a contact force 115 between the interactive body 114 and the tissue site 112 without the application of an external force, such as, without limitation, a force that may be generated by a machine or a chemical. The contact force 115 may be exerted on the tissue site 112 through the interactive body 114, and may be directed toward, into, or along a surface or bed 140 of the tissue site 112. The interactive body 114 may be configured to create the tissue deformation without the application of a reduced pressure from a reduced pressure source, which may allow some tissue sites that are not candidates for reduced pressure therapy to experience an increase in granulation tissue development and healing that conventional wound dressings designed for use without reduced pressure cannot provide. The interactive body 114 may be used with a dressing, incorporated as a component within a dressing, or entirely form a dressing. Accordingly, the interactive body 114 may be used independently or in combination with one or more components of the system 110 as described herein, and thus, components of the system 110 may be omitted as desired to suit a particular tissue site or therapeutic application. The interactive body 114 may be used alone or independently of other component of the system 110 if desired.

As used herein, the term "tissue site" may refer to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. Further, as used throughout this disclosure, "or" does not require mutual exclusivity.

The tissue site 112 may extend through or otherwise involve an epidermis 116, a dermis 118, and a subcutaneous tissue 120. The tissue site 112 may be a sub-surface tissue site as depicted in FIG. 1 that extends below the surface of the epidermis 116. Further, the tissue site 112 may be a surface tissue site (not shown) that predominantly resides on the surface of the epidermis 116. The system 110 may also be utilized without limitation at other tissue sites. Further, the tissue site 112 may have an edge 122 or perimeter defining an outer boundary of the tissue site 112. Other tissue, such as the epidermis 116, may reside beyond the edge 122 of the tissue site 112, and may surround the tissue site 112.

In some embodiments, the system 110 may include a sealing member 128, which may also be referred to herein as a moisture barrier 129. The sealing member 128 or the moisture barrier 129 may be configured to provide a sealed space 130 between the sealing member 128 or the moisture barrier 129 and the tissue site 112. The interactive body 114 may be configured to be positioned in the sealed space 130.

The sealing member 128 or the moisture barrier 129 may be formed from a material that allows for a fluid seal. A fluid seal may be a seal adequate to protect the tissue site 112 from contaminants. The sealing member 128 or the moisture barrier 129 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M TEGADERM® drape; a polyurethane (PU) drape, such as one available from Avery Dennison Corporation of Pasadena, Calif.; polyether block polyamide copolymer (PEBAX), for example, from Arkema, France; Expopack 2327; or other appropriate material.

The sealing member 128 or the moisture barrier 129 may be vapor permeable and liquid impermeable, thereby allowing some vapor to exit the sealed space 130 while inhibiting the exit of liquids. Although some embodiments of the sealing member 128 or the moisture barrier 129 may be breathable and allow some vapor to permeate or pass through, the sealing member 128 or the moisture barrier 129 may be configured to trap, retain, or hold moisture at the tissue site 112. For example, the sealing member 128 or the moisture barrier 129 may be configured to maintain an amount of moisture or humidity at the tissue site 112 that is higher than ambient moisture or humidity levels external to the sealing member 128, the moisture barrier 129, the sealed space 130, or the tissue site 112. In some embodiments, the sealing member 128 and the moisture barrier 129 may be configured to suppress, prevent, or eliminate the passage of vapor and liquid from the tissue site 112, through the sealing member 128 or the moisture barrier 129. Further, in some embodiments, the sealing member 128 or the moisture barrier 129 may be entirely impermeable to vapor and liquid.

In some embodiments, the sealing member 128 or the moisture barrier 129 may be a film layer, adhesive film, membrane, coating, or sheet. The sealing member 128 or the moisture barrier 129 may include a range of medically suitable films having a thickness between about 15 microns (μm) to about 50 microns (μm). In some embodiments, the sealing member 128 or the moisture barrier 129 may be configured to cover an exterior-facing surface 131 of the interactive body 114 facing away from or outward from the tissue site 112. Further, in some embodiments, the sealing member 128 or the moisture barrier 129 may be a coating or layer adhered to or forming part of the exterior-facing surface 131 of the interactive body 114 that is configured to face away or outward from the tissue site 112.

In some embodiments, the sealing member 128 or the moisture barrier 129 may be deployed with an adhesive 132 or bonding agent to secure and seal the sealing member 128 or the moisture barrier 129 to tissue at or around the tissue site 112, such as the epidermis 116. For example, the adhesive 132 or bonding agent may be positioned between the sealing member 128 or the moisture barrier 129 and tissue or the epidermis 116 around the tissue site. The adhesive 132 or bonding agent may be any medically acceptable adhesive or agent, such as an acrylic adhesive. In some embodiments, the adhesive 132 or bonding agent may form at least part of a surface of the sealing member 128 or the moisture barrier 129, such as a coating, configured to face the tissue site 112 or tissue around the tissue site 112 or the exterior-facing surface 131 of the interactive body 114. In some embodiments, the adhesive 132 or bonding agent may be a separate component or layer of material, such as, for example, a hydrogel that may be positioned between the sealing member 128 or the moisture barrier 129 and the tissue site 112 or tissue around the tissue site 112. Although the sealing member 128 or the moisture barrier 129 may extend beyond or outward from the edge 122 of the tissue site 112 and a periphery or a boundary of the interactive body 114 as shown in FIG. 1, in some embodiments, the sealing member 128 or the moisture barrier 129 may reside within the periphery or outer boundary of the interactive body 114.

Figure 2:
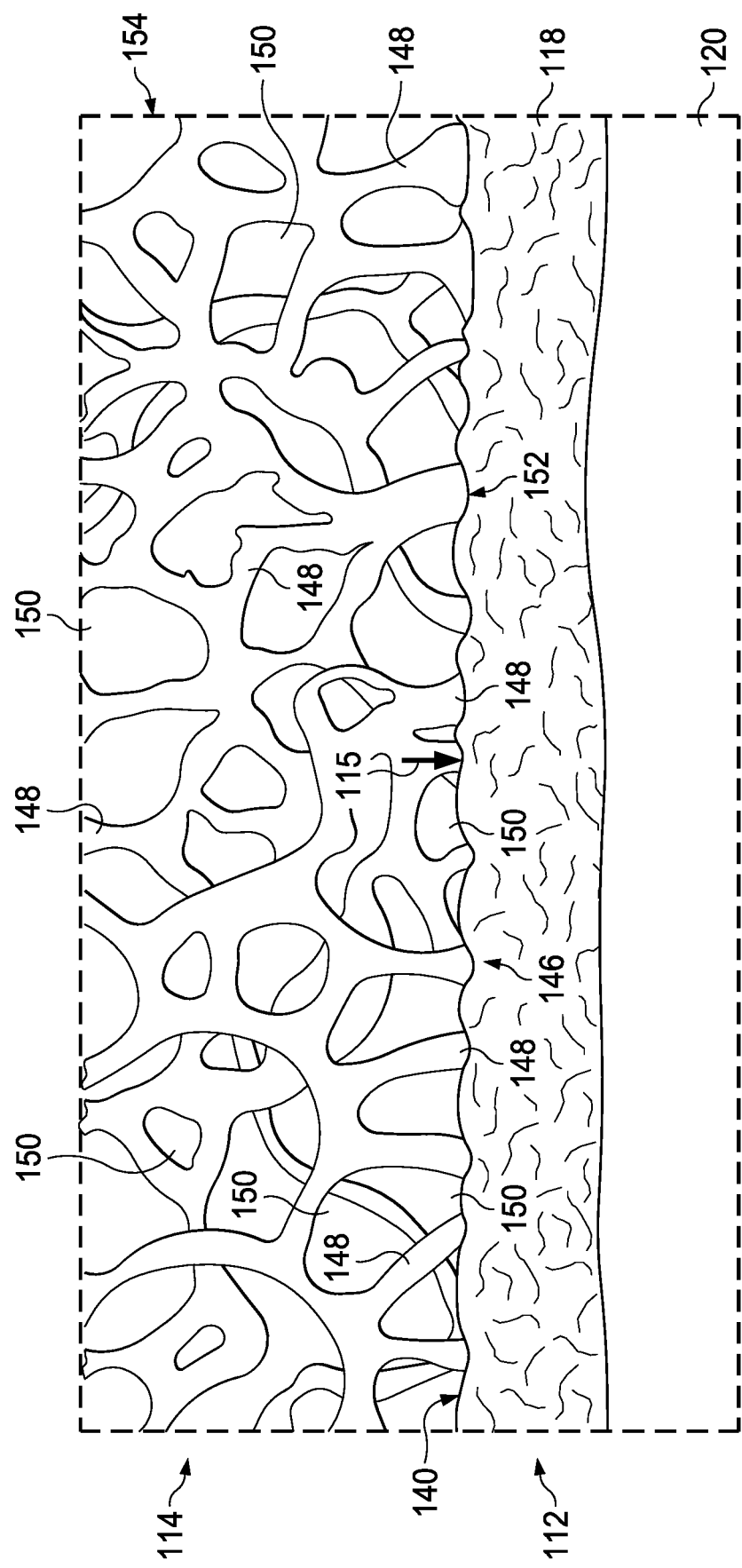
FIG. 2 is a detail view of an illustrative example of a tissue contact surface of the interactive body of FIG. 1 in contact with the tissue site, taken at reference FIG. 2 shown in FIG. 1.

The interactive body 114 may have a thickness 144 as shown in FIG. 1. Referring to FIG. 2, in some embodiments, the interactive body 114 may include a tissue contact surface 146, a plurality of struts 148, a plurality of voids 150, a tissue interface pattern 152, and a body mass 154. The plurality of voids 150 may be cells, openings, or spaces distributed among the plurality of struts 148. The tissue interface pattern 152 may be defined on the tissue contact surface 146 by a measurement, ratio, fraction, or comparison of an amount of the struts 148 to the voids 150 positioned on the tissue contact surface 146. The body mass 154 may be defined by the size and material properties of the interactive body 114. In some embodiments, the interactive body 114 may include or be formed of a porous substrate material, having a suitable porosity as described herein, that may be fluid permeable. Further, in some embodiments, the interactive body 114 may include or be formed of a hydrophobic material. The hydrophobic material may prevent the interactive body 114 from directly absorbing fluid, such as exudate, from the tissue site 112, but allow the fluid to pass through.

The interactive body 114 may also act as a manifold. The term manifold may refer to a substance or structure configured for delivering fluids to or removing fluids from a tissue site through a plurality of voids, pores, pathways, or flow channels. The plurality of voids, pores, pathways, or flow channels may be interconnected to improve the distribution of fluid provided to and removed from an area around the manifold. Examples of manifolds may include, without limitation, devices that have structural elements arranged to form flow channels, cellular foam, such as closed-cell or open-cell foam, porous tissue collections, sintered polymers, and liquids, gels, and foams that include or cure to include flow channels.

The term porosity may refer to a measurement, ratio, fraction, or comparison of an amount of the struts 148 relative to the voids 150 in the interactive body 114. The plurality of struts 148 and the plurality of voids 150 may be defined by a porosity. Similarly, the tissue interface pattern 152 may be defined by a porosity of the interactive body 114 at the tissue contact surface 146. Porosity, also known as pore density, may be measured in Pores Per Inch (PPI), which designates the number of pores in one linear inch. Although porosity and pore density may be used to describe a porous material, such as foam, these principles may apply to other non-foam structures that include a void space.

In some embodiments, the interactive body 114 may include a porous foam or be formed of a foam. For example, in some embodiments, the foam may be a hydrophobic, reticulated, open-cell polyurethane or polyether foam that may be fluid permeable. Further, in some embodiments, ionic silver may be added to the foam by, for example, a micro bonding process. Other substances, such as antimicrobial agents, may be added to the foam as well.

In some embodiments, a non-reticulated foam or a foam comprised of biocompatible materials other than polyurethane may be used. In one embodiment, a bioabsorbable foam or other porous substrate may be employed. Examples of other materials that may be suitable porous foams or porous substrates include those formed from acrylics, acrylates, thermoplastic elastomers (for example, styrene ethylene butene styrene (SEBS) and other block copolymers), polyether block polyamide (PEBAX), silicone elastomers, poly caprolactam, poly lactic acid, and polyolefins, such as polythene and polypropylene. Still other biocompatible materials may be used if capable of being formed or otherwise made into a porous substrate as described herein.

In some embodiments, the tissue contact surface 146 of the interactive body 114 may have a porosity between about 20 pores per inch to about 80 pores per inch, and in particular embodiments, a porosity between about 40 pores per inch to about 50 pores per inch. In embodiments of the interactive body 114 that use a foam, the foam may similarly have a porosity between about 20 pores per inch to about 80 pores per inch, and in particular embodiments, a porosity between about 40 pores per inch to about 50 pores per inch. In some embodiments, the foam may be positioned at the tissue contact surface 146 of the interactive body 114 or form the tissue contact surface 146 of the interactive body 114. The foam may carry the plurality of struts 148 and the plurality of voids 150.

The tissue contact surface 146 of the interactive body 114 may be configured to contact the tissue site 112. In some embodiments, the interactive body 114, such as a porous foam, may be configured to remain at the tissue site 112 for at least three days. In some embodiments, the interactive body 114, such as a porous foam, may be configured to remain at the tissue site 112 between three days to seven days. In some embodiments, the interactive body 114 may be sized to fit within the edge 122 or outer boundary of the tissue site 112 such that the interactive body 114 does not overlap or contact tissue around the tissue site, such as the epidermis 116. The plurality of struts 148 and the plurality of voids 150 may be exposed at the tissue contact surface 146. The plurality of struts 148 and the plurality of voids 150 may be configured to be positioned in direct physical contact with the tissue site 112. At least the plurality of struts 148 may be configured to engage the tissue site 112 and to create tissue deformation at the tissue site 112. As the tissue site 112 deforms, stretches, or moves in response to the plurality of struts 148, tissue at the tissue site 112 may be deformed, stretched, or moved to fill at least a portion of a volume of the voids 150. Accordingly, the voids 150 may engage the tissue site 112, without limitation, by operation of tissue being deformed, stretched, or moved into the voids 150. The plurality of struts 148 and the plurality of voids 150 at the tissue contact surface 146 may collectively define the tissue interface pattern 152. The tissue interface pattern 152 may be configured to engage the tissue site 112 analogous to the plurality of struts 148 and the plurality of voids 150.

For example, the interactive body 114 may provide the contact force 115 at least between the plurality of struts 148 and the tissue site 112 to create the tissue deformation without the application of an external force, such as reduced pressure. The struts 148 and the voids 150 carried on the tissue contact surface 146 may be urged toward the bed 140 of the tissue site 112 under the contact force 115. The contact force 115 may be created in part by the body mass 154 of the interactive body 114, which may be enhanced by other components of the system 110, such as, for example, the sealing member 128 or the moisture barrier 129. As the tissue contact surface 146 moves toward the bed 140, each of the struts 148 may create a stress substantially normal or orthogonal to the bed 140 of the tissue site 112, creating a distribution of deformation or strain across the bed 140 of the tissue site 112. As a result of this deformation or strain, tissue in the bed 140 may be deformed, stretched, or moved into the voids 150 as shown in FIG. 2.

For clarity, the contact force 115 is directed toward or into the bed 140 of the tissue site 112, and distributed across the bed 140, as shown in FIGS. 1 and 2. In some embodiments, the sealing member 128 or the moisture barrier 129 may enhance or increase the contact force 115. For example, the sealing member 128 or the moisture barrier 129 may have elastic properties capable of generating a potential energy or force when the sealing member 128 or the moisture barrier 129 is stretched or expanded to a stretched state. In such an embodiment, the potential energy or stored force in the sealing member 128 or the moisture barrier 129 may be imparted to the interactive body 114 or the tissue site 112 when the sealing member 128 or moisture barrier 130 attempts to return to a relaxed state after being stretched across and coupled to the tissue site 112 or the interactive body 114 in the stretched state.

As described herein, the tissue interface pattern 152 may be defined by the plurality of struts 148 and the plurality of voids 150 at the tissue contact surface 146. The tissue interface pattern 152 may be selectable according to the body mass 154, and the body mass 154 may be selectable according to the tissue interface pattern 152. For example, the tissue interface pattern 152 may be selected such that the plurality of struts 148 exposed at the tissue contact surface 146 have a shape or a surface area sized to create tissue deformation under the contact force 115 provided by the interactive body 114. The surface area of the plurality of struts 148 exposed at the tissue contact surface 146 may decrease as the size of the plurality of voids 150 increases.

By way of example, a low porosity material having a porosity of 10 pores per inch will have a larger average void size or pore size compared to a high porosity material having a porosity of 60 pores per inch. Herein, a low porosity material may be a material that has a lower amount of pores per inch than a high porosity material having a higher amount of pores per inch. In a low porosity material, the larger size of the voids 150 or pores may occupy more space than the plurality of struts 148 in the tissue interface pattern 152, thereby reducing the surface area of the plurality of struts 148 exposed at the tissue contact surface 146 for engaging the tissue site 112. The plurality of struts 148 having a reduced surface area may require less of the contact force 115 to produce a desired amount of tissue deformation since the contact force 115 of this example will be exerted by a smaller surface area of the tissue interface pattern 152.

Figure 3A:
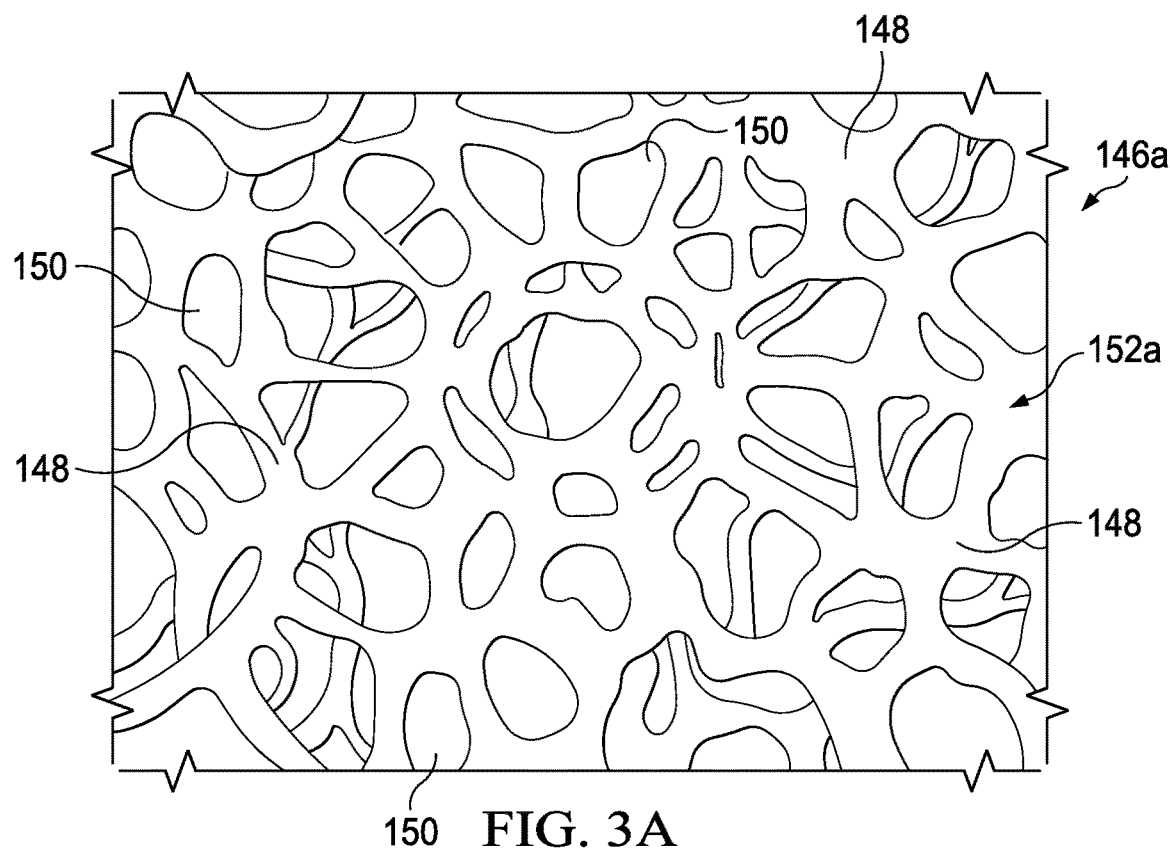
FIG. 3A is a cross-sectional, detail view of another illustrative example of an interactive body.
Figure 3B:
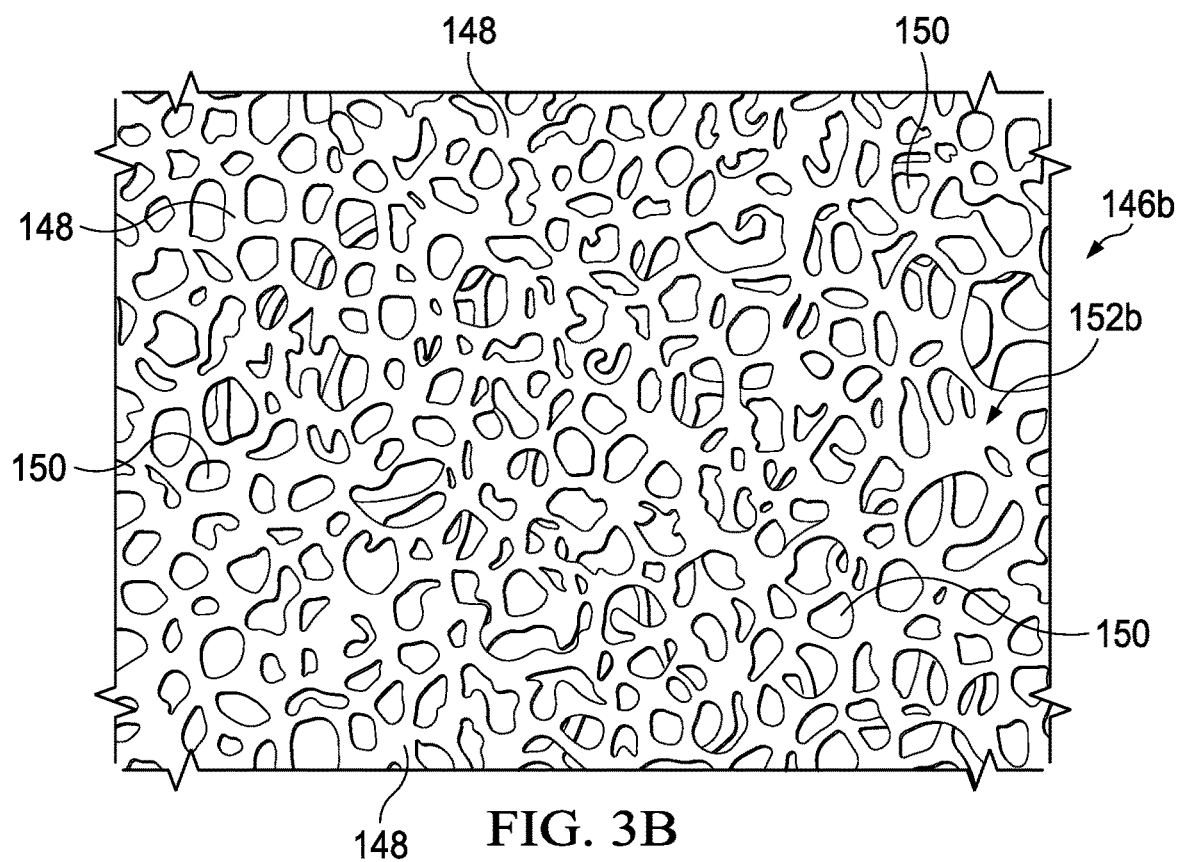
FIG. 3B is a cross-sectional, detail view of another illustrative example of an interactive body.
Figure 3C:
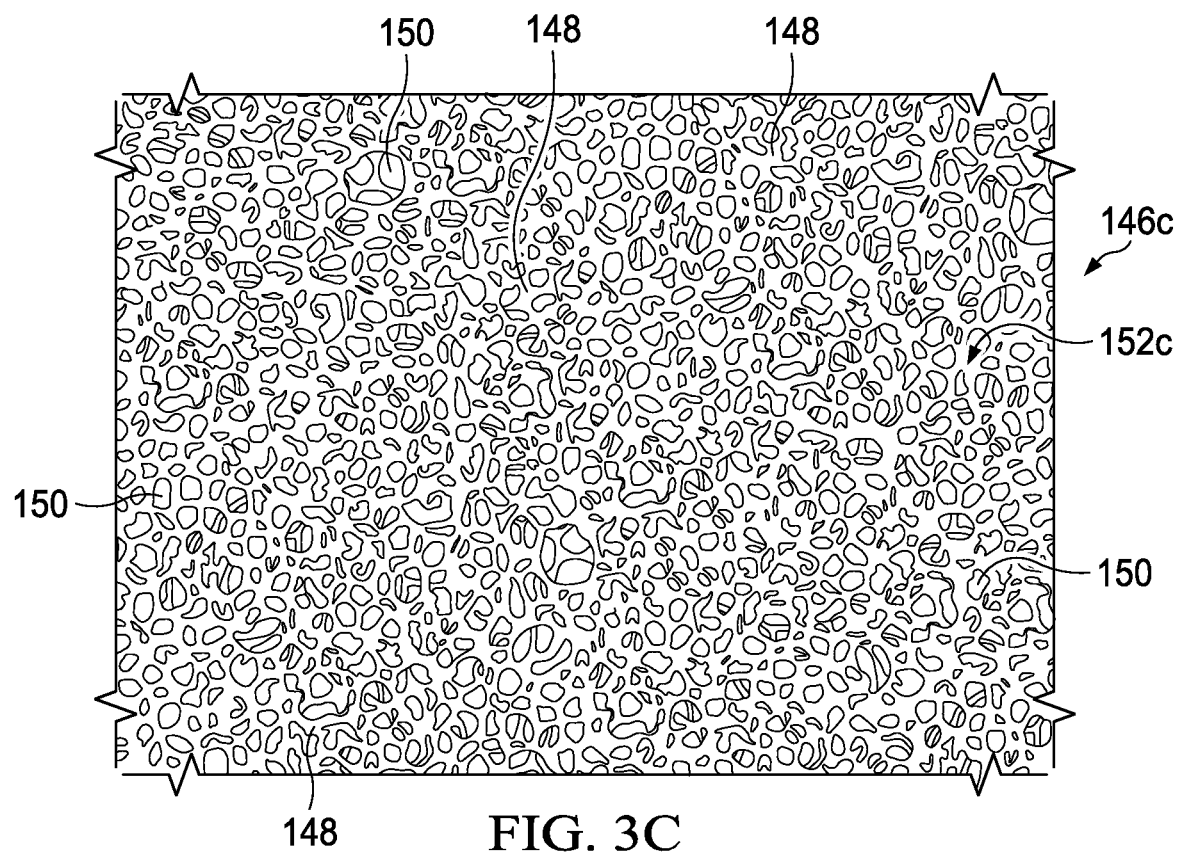
FIG. 3C is a cross-sectional, detail view of another illustrative example of an interactive body.

For example, FIGS. 3A-3C illustrate how variations in the porosity at the tissue contact surface 146 of the interactive body 114 can define the tissue interface pattern 152. In FIG. 3A, in some illustrative embodiments, the tissue contact surface 146 may be a tissue contact surface 146a, and the tissue interface pattern 152 may be a tissue interface pattern 152a. The tissue contact surface 146a may have a porosity of 40 pores per inch, which may define the tissue interface pattern 152a having the shape and surface area of the struts 148 and the voids 150 shown in FIG. 3A.

In FIG. 3B, in some illustrative embodiments, the tissue contact surface 146 may be a tissue contact surface 146b, and the tissue interface pattern 152 may be a tissue interface pattern 152b. The tissue contact surface 146b may have a porosity of 45 pores per inch, which may define the tissue interface pattern 152b having the shape and surface area of the struts 148 and the voids 150 shown in FIG. 3B. The struts 148 exposed at the tissue contact surface 146b in the tissue interface pattern 152b in FIG. 3B have a greater surface area than the struts 148 exposed at the tissue contact surface 146a in the tissue interface pattern 152a in FIG. 3A. Accordingly, the contact force 115 required for the tissue interface pattern 152b may be greater than the tissue interface pattern 152a to produce a desired amount of tissue deformation.

In FIG. 3C, in some illustrative embodiments, the tissue contact surface 146 may be a tissue contact surface 146c, and the tissue interface pattern 152 may be a tissue interface pattern 152c. The tissue contact surface 146c may have a porosity of 50 pores per inch, which may define the tissue interface pattern 152c having the shape and surface area of the struts 148 and the voids 150 shown in FIG. 3C. The struts 148 exposed at the tissue contact surface 146c in the tissue interface pattern 152c in FIG. 3C have a greater surface area than the struts 148 exposed at the tissue contact surface 146b in the tissue interface pattern 152b in FIG. 3B and the tissue contact surface 146a in the tissue interface pattern 152a in FIG. 3A. Accordingly, the contact force 115 required for the tissue interface pattern 152c may be greater than the tissue interface pattern 152b and the tissue interface pattern 152a to produce a desired amount of tissue deformation.

The body mass 154 may be configured to create a desired amount of tissue deformation in combination with the tissue interface pattern 152. The body mass 154 may be selectable according to the tissue interface pattern 152. For example, the body mass 154 may be selected by material properties or sized sufficiently to create a desired amount of tissue deformation with the tissue interface pattern 152. Alternatively, the tissue interface pattern 152 may be selected appropriately according to the size or material properties of the body mass 154. In some embodiments, the body mass 154 may correspond to a weight that may provide the contact force 115 of the interactive body 114, which may be enhanced by other components of the system 110, such as the previously described the sealing member 128 or the moisture barrier 129, Herein, the body mass 154 and the weight of the body mass 154 may be defined or selected according to the thickness 144 of the interactive body 114. The thickness 144 of the interactive body 114 may also be the same as a thickness of the body mass 154. In some embodiments, the thickness 144 of the body mass 154 or the interactive body 114 may be substantially the same as a depth that the bed 140 extends into the tissue site 112. In some embodiments, the thickness 144 of the body mass 154 or the interactive body 114 may be substantially flush or even with the surface of the epidermis 116 or the edge 122 of the tissue site 112. In some embodiments, the thickness 144 of the body mass 154 or the interactive body 114 may be between about 2 millimeters to about 8 millimeters. In some particular embodiments, the thickness 144 of the body mass 154 or the interactive body 114 may be about 5 millimeters.

Continuing with the discussion of FIGS. 3A-3C, a surface area of the struts 148 in the tissue interface patterns 152a-c were described for a range of porosities at the tissue contact surfaces 146a-c, respectively. A greater contact force 115 may be required from the interactive body 114 to produce a set amount of tissue deformation for embodiments of the tissue interface pattern 152 having a greater surface area of the struts 148 or a higher porosity at the tissue contact surface 146. For embodiments of the tissue interface pattern 152 having a greater surface area of the struts 148 or a higher porosity at the tissue contact surface 146, the thickness 144 or weight of the body mass 154 may be increased to increase the contact force 115 of the interactive body 114 sufficiently to create the tissue deformation.

A system, dressing, or method employing the interactive body 114 according to this disclosure may stimulate tissue growth, providing a wound bed ready for grafting or epithelialization without the application of an external force, such as a compressive force, that may be associated with the application of conventional negative pressure wound therapy (NPWT). Conventional dressings that do not use negative pressure, referred to as non-NPWT dressings, typically use non-adherent interface layers, silicones, and similar elements to make them non-adherent to the tissue, less susceptible to tissue in-growth, and less likely to cause tissue disruption. Accordingly, non-NPWT dressings are typically designed to reduce or eliminate mechanical interaction with tissue, limiting their ability to stimulate tissue growth.

NPWT dressings may be designed to mechanically interact with tissue as a result of compressive and other forces applied to the tissue through the dressing by negative pressure generated by a negative pressure source. Being designed for use with negative pressure, these NPWT dressings do not typically produce sufficient mechanical interaction with tissue to stimulate or accelerate tissue growth without the application of negative pressure. In contrast, the interactive body 114 is configured as described herein to directly contact and interact with the bed 140 of the tissue site 112 to stimulate growth without negative pressure. Further, the interactive body 112 is configured to be used without an absorbent material and with the sealing member 128 or the moisture barrier 129 to maintain increased moisture levels at the tissue site for enhanced healing.

Referring to testing results shown in FIGS. 4A-4D, various configurations and test articles for the system 110 and the interactive body 114 were tested. The test articles had varying void or pore sizes, material compositions, and structural features. The pore or void sizes varied from about 20 pores per inch to about 80 pores per inch. The materials tested included foams, such as ester-based and ether-based polyurethane foams; polyvinylalcohol foams; silicone; collagen compositions; and collagen coatings. The structures tested included varying mass or thickness; protrusions, such as silicone protrusions; bed-of-nails features; the addition of absorbent layers and compounds; and the addition of sealing layers or members, such as a medical drape. The testing sought a material, structure, and pore size for use as a dressing or with a dressing that would optimize the formation of granulation tissue at a tissue site, the quality of the granulation tissue, and the speed in which the granulation tissue is formed without the application of negative pressure.

Figure 4A:
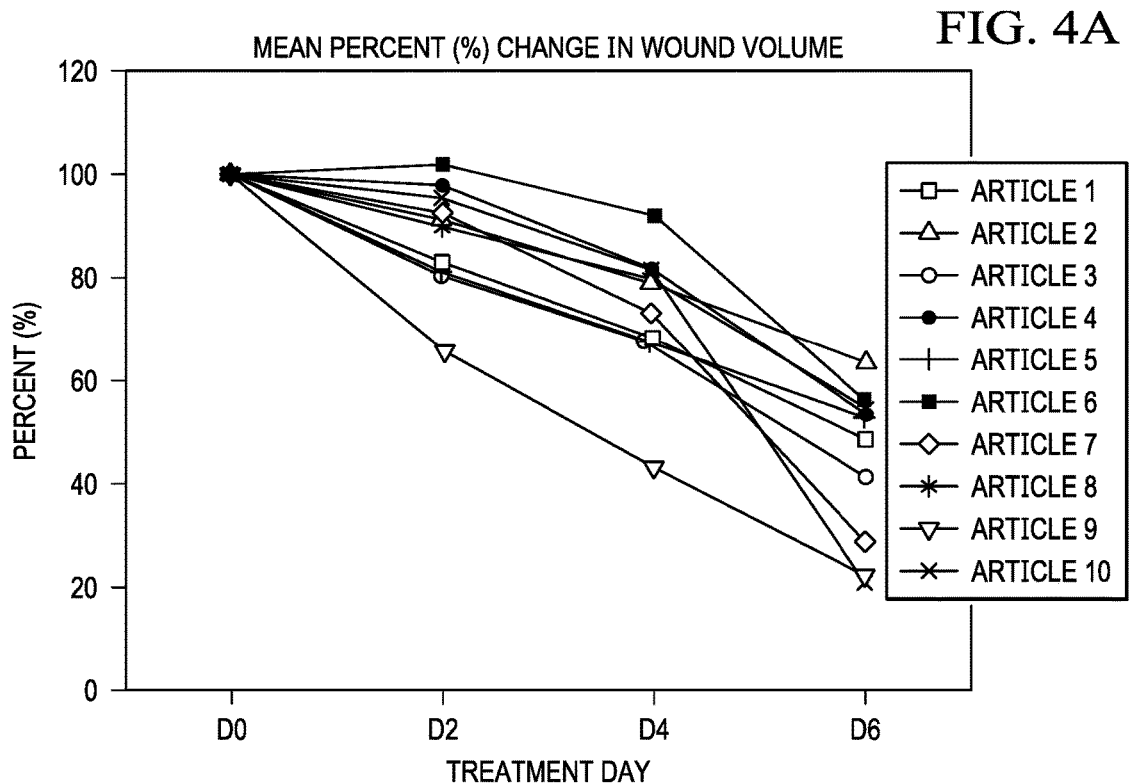
FIG. 4A is a plot of Mean Percent Change in Wound Volume for Articles 1-10 over a six day testing period.
Figure 4B:
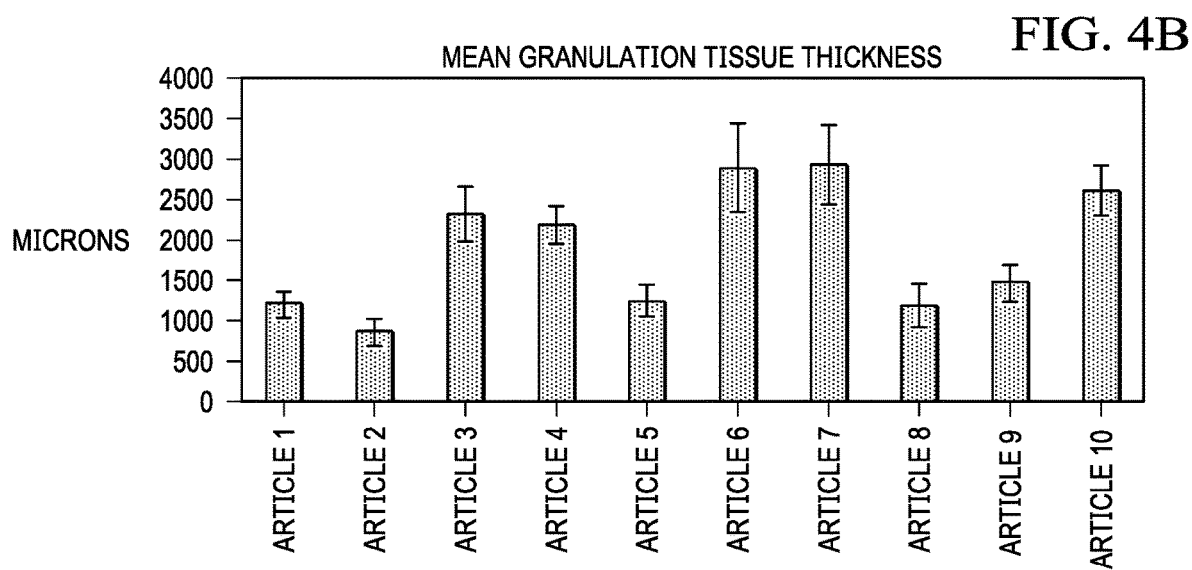
FIG. 4B is a bar graph of Mean Granulation Tissue Thickness for Articles 1-10, measured in microns, over a six day testing period.
Figure 4C:
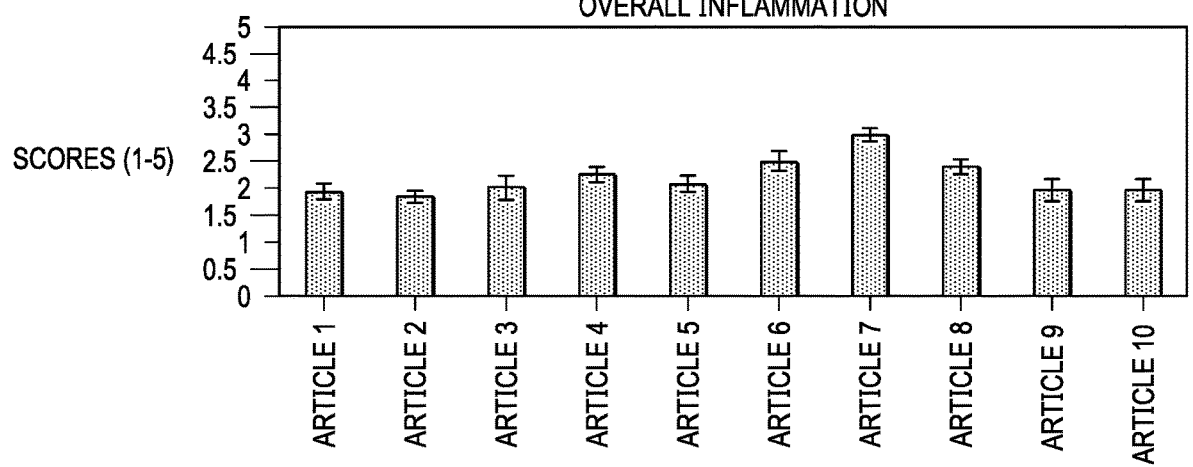
FIG. 4C is a bar graph of Overall Inflammation for Articles 1-10, scored from 1-5, over a six day testing period.
Figure 4D:
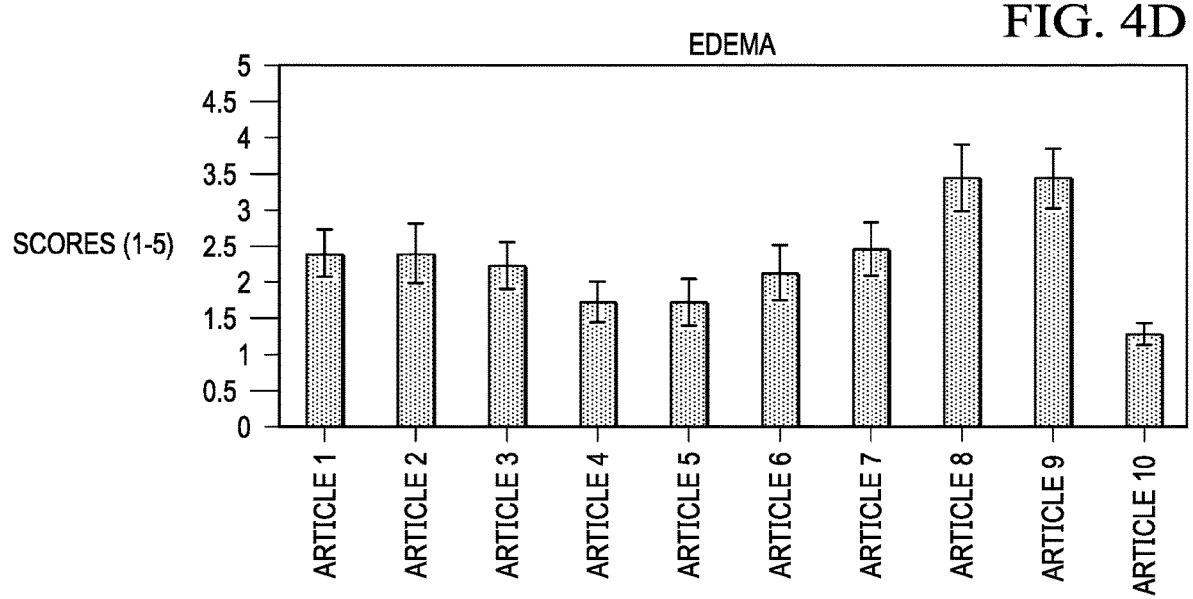
FIG. 4D is a bar graph of Edema for Articles 1-10, scored from 1-5, over a six day testing period.
Figure 5A:
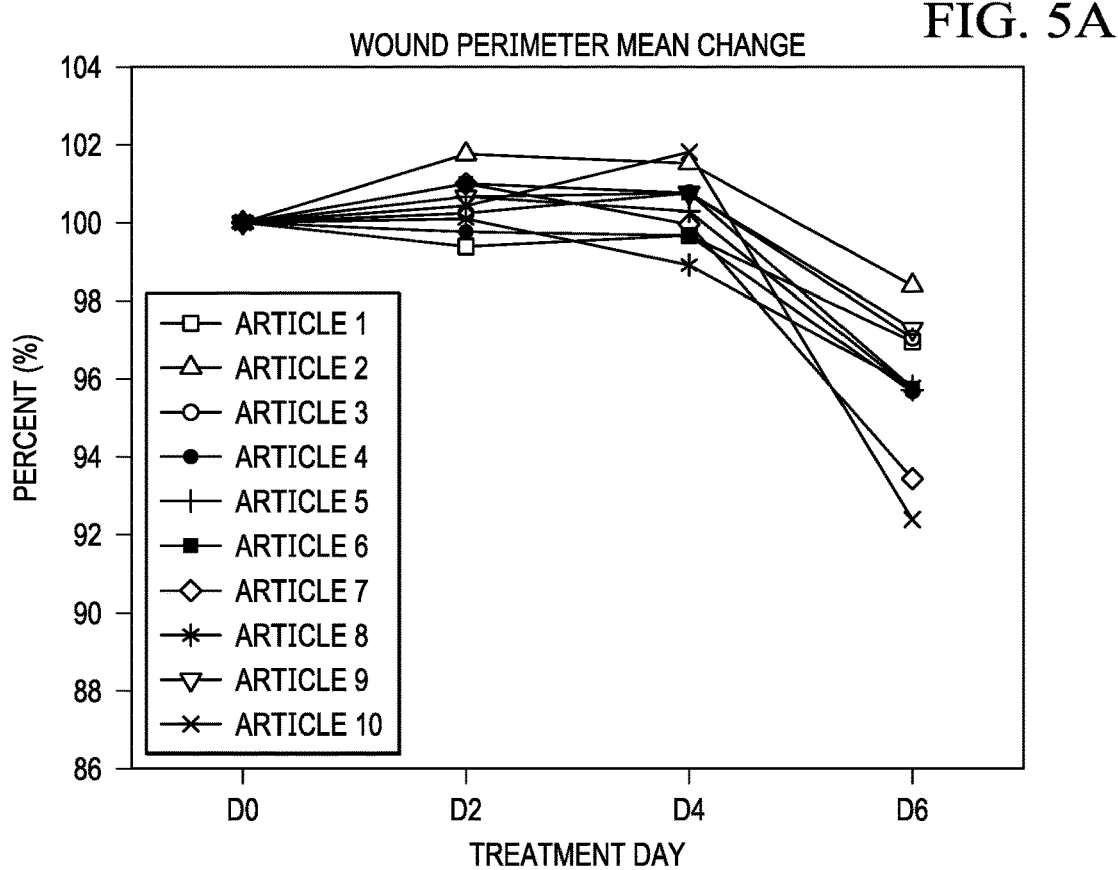
FIG. 5A is a plot of Wound Perimeter Mean Change for Articles 1-10 over a six day testing period.
Figure 5B:
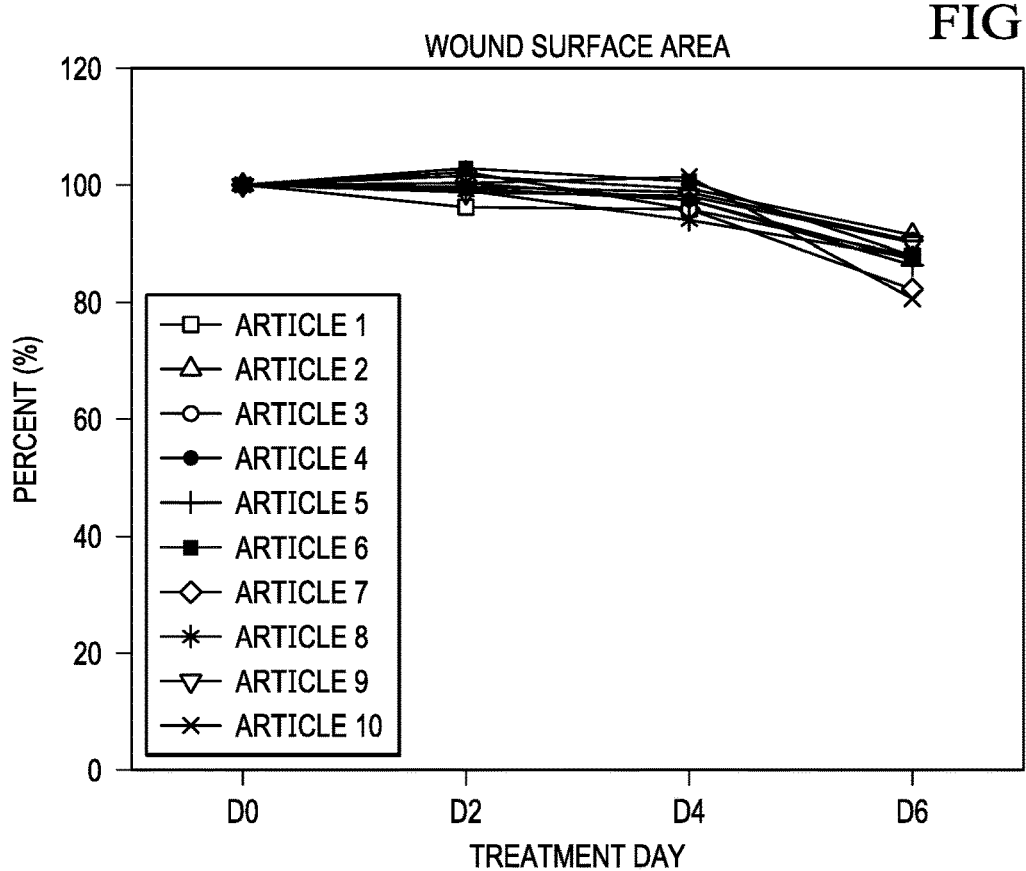
FIG. 5B is a plot of Wound Surface Area for Articles 1-10 over a six day testing period.

FIG. 4A is a plot of Mean Percent Change in Wound Volume for Articles 1-10 over a six day testing period. FIG. 4B is a bar graph of Mean Granulation Tissue Thickness for Articles 1-10, measured in microns, over a six day testing period. FIG. 4C is a bar graph of Overall Inflammation for Articles 1-10, scored from 1-5, over a six day testing period. FIG. 4D is a bar graph of Edema for Articles 1-10, scored from 1-5, over a six day testing period. FIG. 5A is a plot of Wound Perimeter Mean Change for Articles 1-10 over a six day testing period; and FIG. 5B is a plot of Wound Surface Area for Articles 1-10 over a six day testing period. Referring to FIGS. 4C-4D, Overall Inflammation and Edema were scored from 1-5 as follows: Score 0 indicating no edema; Score 1 indicating minimal edema; Score 2 indicating mild edema; Score 3 indicating moderate edema; Score 4 indicating marked or significant edema; and Score 5 indicating severe edema.

The test results show that the system 110 and the interactive body 114 according to this disclosure, shown as Test Article 10, produced the greatest percent change or reduction in wound volume (FIG. 4A), wound perimeter (FIG. 5A), and wound surface area (FIG. 5B), while exhibiting excellent granulation tissue development (FIG. 4B), excellent reduction in inflammation (FIG. 4C), and acceptable reduction in edema (FIG. 4D). Accordingly, the system 110 provides a solution for stimulating the formation of quality granulation tissue, without the application of negative pressure or an absorbent material, compared to conventional dressings and systems.

In some illustrative, non-limiting examples a method for stimulating tissue growth at a tissue site may include providing the interactive body 114 including the tissue contact surface 146. The tissue contact surface 146 may include the plurality of struts 148 and the plurality of voids 150 exposed at the tissue contact surface 146. Further, the method may include positioning the tissue contact surface 146 in contact with the tissue site 112, and engaging the plurality of struts 148 and the plurality of voids 150 with a tissue at the tissue site 112 to create the contact force 115 on the tissue. Further, the method may include covering the interactive body 114 at the tissue site 112 with the sealing member 128 or the moisture barrier 129 configured to trap moisture at the tissue site 112, and deforming the tissue at the tissue site 112 by operation of the contact force 115 without an application of a reduced pressure.

The interactive body 114 may be configured to remain at the tissue site 112 between 3 days to 7 days. In some embodiments, the method may include removing the interactive body 114 from the tissue site 112 between 3 days to 7 days after positioning the tissue contact surface 146 in contact with the tissue site 112. In some embodiments, the method may include leaving the interactive body 114 in contact with the tissue site 112 for at least 3 days.

The sealing member 128 or the moisture barrier 129 may be configured to provide the sealed space 130 between the sealing member 128 or the moisture barrier 129 and the tissue site 112. In some embodiments, the sealing member 128 or the moisture barrier 129 may be configured to maintain an amount of moisture or humidity at the tissue site 112 that is higher than an ambient moisture or humidity level external to the sealing member 128 or the moisture barrier 129. In some embodiments, the sealing member 128 or the moisture barrier 129 may be configured to suppress the passage of vapor and liquid from the tissue site 112.

In some embodiments, the method may include covering the interactive body 114 at the tissue site 112 with the sealing member 128 or the moisture barrier 129. The sealing member 128 or the moisture barrier 129 may be configured to provide the sealed space 130 between the sealing member 128 or the moisture barrier 129 and the tissue site 112. Further, the sealing member 128 or the moisture barrier 129 may be configured to trap or retain moisture at the tissue site 112.

In some embodiments, the interactive body 114 may include the body mass 154, and the plurality of struts 148 and the plurality of voids 150 may define the tissue interface pattern 152 as described herein. In such embodiments, the method may include selecting the body mass 154 to produce the contact force 115 for deforming the tissue in combination with the tissue interface pattern 152. Selecting the body mass 154 may include sizing the body mass 154 to have a weight sufficient to produce the contact force 115 for deforming the tissue in combination with the tissue interface pattern 152.

In some embodiments, the method may include configuring the tissue interface pattern 152 to produce the contact force 115 for deforming the tissue in combination with the body mass 154. Configuring the tissue interface pattern 152 may include sizing the plurality of voids 150 and the plurality of struts 148 to produce the contact force 115 for deforming the tissue in combination with the body mass 154.

In some embodiments, the method may include determining a size of the body mass 154 to produce the contact force 115 as a function of a shape, geometry, or surface area of the tissue interface pattern 152. In some embodiments, the method may include determining a geometry or a surface area of the tissue interface pattern 152 to produce the contact force 115 as a function of a size of the body mass 154.

In some embodiments, the interactive body 114 may include or be formed of a porous foam carrying the plurality of struts 148 and the plurality of voids 150 at the tissue contacting surface 146 as described herein. In some embodiments, the method may include selecting the porous foam to have a porosity configured to create the contact force 115 for deforming the tissue. In some embodiments, the method may include selecting the porous foam to have a porosity according to a granulation tissue formation rate desired at the tissue site 112. A decrease in the porosity may produce a larger pore size, which may correspond to an increase in the granulation tissue formation rate as described herein. For example, in some embodiments, the porosity of the porous foam may be between about 40 pores per inch to about 50 pores per inch.

While many of the apparatus, systems, and methods described herein have been illustrated for use with tissue sites or wounds that are at or near the epidermis of a patient, the apparatus, systems, and methods may similarly be used to treat subcutaneous tissue sites, tunnel wounds, or other undermined areas of tissue.

Although the subject matter of this disclosure has been provided by way of example in the context of certain illustrative, non-limiting example embodiments, various changes, substitutions, permutations, and alterations can be made without departing from the scope of this disclosure as defined by the appended claims. Any feature described in connection to any one example embodiment may also be applicable to any other example embodiment. As such, the benefits and advantages described above may relate to one example embodiment or may relate to several example embodiments. Further, the steps of the methods described herein may be carried out in any suitable order, or simultaneously, where appropriate.

What is claimed is:

1. A non-negative pressure system for stimulating tissue growth at a tissue site, comprising:
a porous foam comprising an exterior-facing surface, a tissue contact surface, and a plurality of struts positioned at the tissue contact surface, the plurality of struts of the porous foam configured to directly contact the tissue site and to create tissue deformation at the tissue site, the porous foam being formed of a hydrophobic material configured to prevent fluid absorption within the porous foam such that the porous foam is entirely non-absorbent;
a moisture barrier configured to cover the exterior-facing surface of the porous foam;
wherein the porous foam comprises a porosity of 20 to 35 pores per inch such that the porous foam is configured to provide a contact force at least between the plurality of struts and the tissue site to stretch and move tissue into voids positioned among the plurality of struts without the application of a reduced pressure; and
wherein the moisture barrier is configured to trap moisture at the tissue site.

2. The system of claim 1, wherein the porous foam is configured to remain at the tissue site for at least 3 days.

3. The system of claim 1, wherein the porous foam is configured to remain at the tissue site between 3 days to 7 days.

4. The system of claim 1, wherein the plurality of struts are exposed at the tissue contact surface.

5. The system of claim 1, further comprising a plurality of voids, and wherein the plurality of voids and the plurality of struts are exposed at the tissue contact surface and configured to engage the tissue site.

6. The system of claim 1, wherein the porous foam comprises a reticulated polyurethane foam.

7. The system of claim 1, wherein the porous foam comprises a thickness that is substantially flush with a surface of an epidermis around the tissue site.

8. The system of claim 1, wherein the moisture barrier comprises a film layer configured to provide a sealed space between the film layer and the tissue site, the porous foam configured to be positioned in the sealed space.

9. The system of claim 8, wherein the film layer comprises an adhesive.

10. The system of claim 1, wherein the moisture barrier comprises an adhesive film.

11. The system of claim 1, wherein the moisture barrier comprises a coating.

* * * * *